United States Patent [19]

Brown

[11] Patent Number: 5,084,556

[45] Date of Patent: Jan. 28, 1992

[54] COMPOSITION OF M-CSF CONJUGATED TO CYTOTOXIC AGENTS AND A METHOD FOR TREATING CANCERS CHARACTERIZED BY OVER-EXPRESSION OF THE C-FMS PROTO-ONCOGENE

[75] Inventor: Eugene L. Brown, Newton Highlands, Mass.

[73] Assignee: Genetics Institute, Inc., Cambridge, Mass.

[21] Appl. No.: 545,678

[22] Filed: Jun. 28, 1990

Related U.S. Application Data

[63] Continuation of Ser. No. 112,801, Oct. 23, 1987.

[51] Int. Cl.$^5$ .............................................. A61K 37/02
[52] U.S. Cl. ..................................... 530/351; 530/402; 530/403; 530/404; 530/405; 424/85.1; 424/85.91; 514/2; 514/8
[58] Field of Search ................. 424/85.1, 85.91; 514/2, 514/8; 530/351, 402, 405

[56] References Cited

U.S. PATENT DOCUMENTS

| | | | |
|---|---|---|---|
| 4,504,586 | 3/1985 | Nicolson | 435/68 |
| 4,545,985 | 10/1985 | Pashan et al. | 424/85.91 |
| 4,675,382 | 6/1987 | Murphy | 530/402 |
| 4,933,288 | 6/1990 | Greenfield | 435/69.5 |

OTHER PUBLICATIONS

Bertelmez et al., *J. Cell. Physiol.*, 122, 1985, pp. 362–378.
Granelli-Piperno et al., *J. Exp. Med.* 163, 1986, pp. 922–937.
Olsnes et al., *Pharma Ther.*, 15, 1982, pp. 355–379.
Clark et al., *Science* 236, 1987, pp. 1229–1237.
Marimato et al., *J. Immunol* 131, 1983, pp. 1726–1764.
Metcalf, *Blood* 67(2), 1986, pp. 257–267.

*Primary Examiner*—Garnette D. Draper
*Attorney, Agent, or Firm*—Luann Cserr; Bruce Eisen

[57] ABSTRACT

A composition and method for treating cancers characterized by over-expression of the c-fms proto-oncogene/M-CSF receptor protein are provided. The composition involves a M-CSF polypeptide cross-linked to a cytotoxic agent capable of crossing into the cytoplasm of the cell bearing the receptor and killing the cell.

5 Claims, 5 Drawing Sheets

Figure 1

```
          10         20         30         40         50         60         70
    CCTGGGTCCT CTOGGCGCCA GAGCCGCTCT CCGCATCCCA GGACAGCGGT GCGGCCCTCG GCCGGGGCGC 80         90        100        110        120        130        140
    CCACTCCGCA GCAGCCAGCG AGCGAGCGAG CGAGCGAGGG CGGCCGACGC GCCCGGCCGG GACCCAGCTG (-32)             160            175             190
    CCCGT ATG ACC GCG CCG GGC GCC GCC GGG CGC TGC CCT CCC ACG ACA TGG CTG
          MET Thr Ala Pro Gly Ala Ala Gly Arg Cys Pro Pro Thr Thr Trp Leu 205                   220                   235          (1)
    GGC TCC CTG CTG TTG TTG GTC TGT CTC CTG GCG AGC AGG AGT ATC ACC GAG GAG
    Gly Ser Leu Leu Leu Leu Val Cys Leu Leu Ala Ser Arg Ser Ile Thr Glu Glu 250                   265                   280                   295
    GTG TCG GAG TAC TGT AGC CAC ATG ATT GGG AGT GGA CAC CTG CAG TCT CTG CAG
    Val Ser Glu Tyr Cys Ser His MET Ile Gly Ser Gly His Leu Gln Ser Leu Gln 310                   325                   340             355
    CGG CTG ATT GAC AGT CAG ATG GAG ACC TCG TGC CAA ATT ACA TTT GAG TTT GTA
    Arg Leu Ile Asp Ser Gln MET Glu Thr Ser Cys Gln Ile Thr Phe Glu Phe Val 370                   385                   400
    GAC CAG GAA CAG TTG AAA GAT CCA GTG TGC TAC CTT AAG AAG GCA TTT CTC CTG
    Asp Gln Glu Gln Leu Lys Asp Pro Val Cys Tyr Leu Lys Lys Ala Phe Leu Leu 415                   430                   445             460
    GTA CAA GAC ATA ATG GAG GAC ACC ATG CGC TTC AGA GAT AAC ACC CCC AAT GCC
    Val Gln Asp Ile MET Glu Asp Thr MET Arg Phe Arg Asp Asn Thr Pro Asn Ala 475                   490                   505
    ATC GCC ATT GTG CAG CTG CAG GAA CTC TCT TTG AGG CTG AAG AGC TGC TTC ACC
    Ile Ala Ile Val Gln Leu Gln Glu Leu Ser Leu Arg Leu Lys Ser Cys Phe Thr 520                   535                   550                   565
    AAG GAT TAT GAA GAG CAT GAC AAG GCC TGC GTC CGA ACT TTC TAT GAG ACA CCT
    Lys Asp Tyr Glu Glu His Asp Lys Ala Cys Val Arg Thr Phe Tyr Glu Thr Pro 580                   595           (122)610                625
    CTC CAG TTG CTG GAG AAG GTC AAG AAT GTC TTT AAT GAA ACA AAG AAT CTC CTT
    Leu Gln Leu Leu Glu Lys Val Lys Asn Val Phe Asn Glu Thr Lys Asn Leu Leu 640                   655                   670
    GAC AAG GAC TGG AAT ATT TTC AGC AAG AAC TGC AAC AAC AGC TTT GCT GAA TGC
    Asp Lys Asp Trp Asn Ile Phe Ser Lys Asn Cys Asn Asn Ser Phe Ala Glu Cys 685                   700                   715             730
    TCC AGC CAA GAT GTG GTG ACC AAG CCT GAT TGC AAC TGC CTG TAC CCC AAA GCC
    Ser Ser Gln Asp Val Val Thr Lys Pro Asp Cys Asn Cys Leu Tyr Pro Lys Ala
```

Figure 1-2

```
          745                      760                      775
ATC CCT AGC AGT GAC CCG GCC TCT GTC TCC CCT CAT CAG CCC CTC GCC CCC TCC
Ile Pro Ser Ser Asp Pro Ala Ser Val Ser Pro His Gln Pro Leu Ala Pro Ser 790                  805(189)              820                      835
ATG GCC CCT GTG GCT GGC TTG ACC TGG GAG GAC TCT GAG GGA ACT GAG GGC AGC
MET Ala Pro Val Ala Gly Leu Thr Trp Glu Asp Ser Glu Gly Thr Glu Gly Ser 850                      865                      880                  895
TCC CTC TTG CCT GGT GAG CAG CCC CTG CAC ACA GTG GAT CCA GGC AGT GCC AAG
Ser Leu Leu Pro Gly Glu Gln Pro Leu His Thr Val Asp Pro Gly Ser Ala Lys 910                      925                      940
CAG CGG CCA CCC AGG AGC ACC TGC CAG AGC TTT GAG CCG CCA GAG ACC CCA GTT
Gln Arg Pro Pro Arg Ser Thr Cys Gln Ser Phe Glu Pro Pro Glu Thr Pro Val 955                      970                      985                  1000
GTC AAG GAC AGC ACC ATC GGT GGC TCA CCA CAG CCT CGC CCC TCT GTC GGG GCC
Val Lys Asp Ser Thr Ile Gly Gly Ser Pro Gln Pro Arg Pro Ser Val Gly Ala 1015                     1030                     1045
TTC AAC CCC GGG ATG GAG GAT ATT CTT GAC TCT GCA ATG GGC ACT AAT TGG GTC
Phe Asn Pro Gly MET Glu Asp Ile Leu Asp Ser Ala MET Gly Thr Asn Trp Val 1060                     1075                     1090                     1105
CCA GAA GAA GCC TCT GGA GAG GCC AGT GAG ATT CCC GTA CCC CAA GGG ACA GAG
Pro Glu Glu Ala Ser Gly Glu Ala Ser Glu Ile Pro Val Pro Gln Gly Thr Glu 1120                     1135                     1150                     1165
CTT TCC CCC TCC AGG CCA GGA GGG GGC AGC ATG CAG ACA GAG CCC GCC AGA CCC
Leu Ser Pro Ser Arg Pro Gly Gly Gly Ser MET Gln Thr Glu Pro Ala Arg Pro 1180                     1195                     1210
AGC AAC TTC CTC TCA GCA TCT TCT CCA CTC CCT GCA TCA GCA AAG GGC CAA CAG
Ser Asn Phe Leu Ser Ala Ser Ser Pro Leu Pro Ala Ser Ala Lys Gly Gln Gln 1225                     1240                     1255                     1270
CCG GCA GAT GTA ACT GGT ACA GCC TTG CCC AGG GTG GGC CCC GTG AGG CCC ACT
Pro Ala Asp Val Thr Gly Thr Ala Leu Pro Arg Val Gly Pro Val Arg Pro Thr 1285                     1300                     1315
GGC CAG GAC TGG AAT CAC ACC CCC CAG AAG ACA GAC CAT CCA TCT GCC CTG CTC
Gly Gln Asp Trp Asn His Thr Pro Gln Lys Thr Asp His Pro Ser Ala Leu Leu 1330                     1345                     1360                     1375
AGA GAC CCC CCG GAG CCA GGC TCT CCC AGG ATC TCA TCA CTG CGC CCC CAG GGC
Arg Asp Pro Pro Glu Pro Gly Ser Pro Arg Ile Ser Ser Leu Arg Pro Gln Gly
```

Figure 1-3

```
        1390                1405                1420                1435
CTC AGC AAC CCC TCC ACC CTC TCT GCT CAG CCA CAG CTT TCC AGA AGC CAC TCC
Leu Ser Asn Pro Ser Thr Leu Ser Ala Gln Pro Gln Leu Ser Arg Ser His Ser 1450                1465                1480
TCG GGC AGC GTG CTG CCC CTT GGG GAG CTG GAG GGC AGG AGG AGC ACC AGG GAT
Ser Gly Ser Val Leu Pro Leu Gly Glu Leu Glu Gly Arg Arg Ser Thr Arg Asp 1495                1510                1525                1540
CGG AGG AGC CCC GCA GAG CCA GAA GGA GGA CCA GCA AGT GAA GGG GCA GCC AGG
Arg Arg Ser Pro Ala Glu Pro Glu Gly Gly Pro Ala Ser Glu Gly Ala Ala Arg 1555                1570                1585
CCC CTG CCC CGT TTT AAC TCC GTT CCT TTG ACT GAC ACA GGC CAT GAG AGG CAG
Pro Leu Pro Arg Phe Asn Ser Val Pro Leu Thr Asp Thr Gly His Glu Arg Gln 1600                1615                1630                1645
TCC GAG GGA TCC TCC AGC CCG CAG CTC CAG GAG TCT GTC TTC CAC CTG CTG GTG
Ser Glu Gly Ser Ser Ser Pro Gln Leu Gln Glu Ser Val Phe His Leu Leu Val 1660                1675                1690                1705
CCC AGT GTC ATC CTG GTC TTG CTG GCT GTC GGA GGC CTC TTG TTC TAC AGG TGG
Pro Ser Val Ile Leu Val Leu Leu Ala Val Gly Gly Leu Leu Phe Tyr Arg Trp 1720                1735                1750
AGG CGG CGG AGC CAT CAA GAG CCT CAG AGA GCG GAT TCT CCC TTG GAG CAA CCA
Arg Arg Arg Ser His Gln Glu Pro Gln Arg Ala Asp Ser Pro Leu Glu Gln Pro 1765                1780                1795                1817
GAG GGC AGC CCC CTG ACT CAG GAT GAC AGA CAG GTG GAA CTG CCA GTG TAGAGGGAAT
Glu Gly Ser Pro Leu Thr Gln Asp Asp Arg Gln Val Glu Leu Pro Val 1827      1837       1847       1857       1867       1877       1887
TCTAAGCTGG ACGCACAGAA CAGTCTCTCC GTGGGAGGAG ACATTATGGG GCGTCCACCA CCACCCCTCC 1897      1907       1917       1927       1937       1947       1957
CTGGCCATCC TCCTGGAATG TGGTCTGCCC TCCACCAGAG CTCCTGCCTG CCAGGACTGG ACCAGAGCAG 1967      1977       1987       1997       2007       2017       2027
CCAGGCTGGG GCCCCTCTGT CTCAACCCGC AGACCCTTGA CTGAATGAGA GAGGCCAGAG GATGCTCCCC 2037      2047       2057       2067       2077       2087       2097
ATGCTGCCAC TATTTATTGT GAGCCCTGGA GGCTCCCATG TGCTTGAGGA AGGCTGGTGA GCCCGGCTCA 2107      2117       2127       2137       2147       2157       2167
GGACCCTCTT CCCTCAGGGG CTGCACCCTC CTCTCACTCC CTTCCATGCC GGAACCCAGG CCAGGGACCC
```

Figure 1-4

```
      2177       2187       2197       2207       2217       2227       2237
ACCGGCCTGT GGTTTGTGGG AAAGCAGGGT GGACGCTGAG GAGTGAAAGA ACCCTGCACC CAGAGGGCCT 2247       2257       2267       2277       2287       2297       2307
GCCTGGTGCC AAGGTATCCC AGCCTGGACA GGCATGGACC TGTCTCCAGA GAGAGGAGCC TGAAGTTCGT 2317       2327       2337       2347       2357       2367       2377
GGGGCGGGAC AGCGTCGGCC TGATTTCCCG TAAAGGTGTG CAGCCTGAGA GACGGAAGA GGAGGCCTCT 2387       2397       2407       2417       2427       2437       2447
GGACCTGCTG GTCTGCACTG ACAGCCTGAA GGGTCTACAC CCTGGCTCA CCTAAGTGCC CTGTGCTGGT 2457       2467       2477       2487       2497       2507       2517
TGCCAGGCGC AGAGGGGAGG CCAGCCCTGC CCTCAGGACC TGCCTGACCT GCCAGTGATG CCAAGAGGGG 2527       2537       2547       2557       2567       2577       2587
GATCAAGCAC TGGCCTCTGC CCCTCCTCCT TCCAGCACCT GCCAGAGCTT CTCCAGGAGG CCAAGCAGAG 2597       2607       2617       2627       2637       2647       2657
GCTCCCCTCA TGAAGGAAGC CATTGCACTG TGAACACTGT ACCTGCCTGC TGAACAGCCT GCCCCCGTCC 2667       2677       2687       2697       2707       2717       2727
ATCCATGAGC CAGCATCCGT CCGTCCTCCA CTCTCCAGCC TCTCCCAGC CTCCTGCACT GAGCTGGCCT 2737       2747       2757       2767       2777       2787       2797
CACCAGTCGA CTGAGGGAGC CCCTCAGCCC TGACCTTCTC CTGACCTGGC CTTTGACTCC CCGGAGTGGA 2807       2817       2827       2837       2847       2857       2867
GTGGGGTGGG AGAACCTCCT GGGCCGCCAG CCAGAGCCGG TCTTTAGGCT GTGTTGTTCG CCCAGGTTTC 2877       2887       2897       2907       2917       2927       2937
TGCATCTTGC ACTTTGACAT TCCAAGAGG GAAGGGACTA GTGGGAGAGA GCAAGGGAGG GGAGGGCACA 2947       2957       2967       2977       2987       2997       3007
GACAGAGAGG CTACAGGGCG AGCTCTGACT GAAGATGGGC CTTTGAAATA TAGGTATGCA CCTGAGGTTG 3017       3027       3037       3047       3057       3067       3077
GGGAGGGTC TGCACTCCCA AACCCCAGCG CAGTGTCCTT TCCCTGCTGC CGACAGGAAC CTGGGGCTGA
```

Figure 1-5

```
         3087       3097       3107       3117       3127       3137       3147
    GCAGGTTATC CCTGTCAGGA GCCCTGGACT GGGCTGCATC TCAGCCCCAC CTGCATGGTA TCCAGCTCCC 3157       3167       3177       3187       3197       3207       3217
    ATCCACTTCT CACCCTTCTT TCCTCCTGAC CTTGGTCAGC AGTGATGACC TCCAACTCTC ACCCACCCCC 3227       3237       3247       3257       3267       3277       3287
    TCTACCATCA CCTCTAACCA GGCAAGCCAG GGTGGGAGAG CAATCAGGAG AGCCAGGCCT CAGCTTCCAA 3297       3307       3317       3327       3337       3347       3357
    TGCCTGGAGG GCCTCCACTT TGTGGCCAGC CTGTGGTGGT GGCTCTGAGG CCTAGGCAAC GAGCGACAGG 3367       3377       3387       3397       3407       3417       3427
    GCTGCCAGTT GCCCCTGGGT TCCTTTGTGC TGCTGTGTGC CTCCTCTCCT GCCGCCCTTT GTCCTCCGCT 3437       3447       3457       3467       3477       3487       3497
    AAGAGACCCT GCCCTACCTG GCCGCTGGGC CCCGTGACTT TCCCTTCCTG CCCAGGAAAG TGAGGGTCGG 3507       3517       3527       3537       3547       3557       3567
    CTGGCCCCAC CTTCCCTGTC CTGATGCCGA CAGCTTAGGG AAGGGCAGTG AACTTGCATA TGGGCTTAG 3577       3587       3597       3607       3617       3627       3637
    CCTTCTAGTC ACAGCCTCTA TATTTGATGC TAGAAAACAC ATATTTTTAA ATGGAAGAAA AATAAAAAGG 3647       3657       3667       3677       3687       3697       3707
    CATTCCCCCT TCATCCCCCT ACCTTAAACA TATAATATTT TAAAGGTCAA AAAAGCAATC CAACCCACTG 3717       3727       3737       3747       3757       3767       3777
    CAGAAGCTCT TTTTGAGCAC TTGGTGGCAT CAGAGCAGGA GGAGCCCCAG AGCCACCTCT GGTGTCCCCC 3787       3797       3807       3817       3827       3837       3847
    CAGGCTACCT GCTCAGGAAC CCCTTCTGTT CTCTGAGAAG TCAAGAGAGG ACATTGGCTC ACGCACTGTG 3857       3867       3877       3887       3897       3907       3917
    AGATTTTGTT TTTATACTTG GAAGTGGTCA ATTATTTTAT ATAAAGTCAT TTAAATATCT ATTTAAAAGA 3927       3937       3947       3957       3967       3977
    TAGGAAGCTG CTTATATATT TAATAATAAA AGAAGTGCAC AAGCTGCCGT TGACGTAGCT CGAG
```

COMPOSITION OF M-CSF CONJUGATED TO CYTOTOXIC AGENTS AND A METHOD FOR TREATING CANCERS CHARACTERIZED BY OVER-EXPRESSION OF THE C-FMS PROTO-ONCOGENE

This application is a continuation of application Ser. No. 07/112,801, filed Oct. 23, 1987.

The present invention refers generally to the treatment of a variety of cancers characterized by the over-expression of the protein receptor, c-fms. More specifically, the invention refers to a composition for such treatment including the M-CSF polypeptide linked to a cytotoxic agent.

BACKGROUND OF THE INVENTION

A variety of oncogenes, proteins present on cancer cells, have been associated with specific cancers. The oncogene fms has come under recent scrutiny as being related to breast, lung pancreatic, ovarian, renal, and possibly other carcinomas, including acute myelocytic leukemia (AML). See, e.g., D. J. Slamon et al, Science, 224:256-262 (1984); C. Walker et al, Proc. Natl. Acad. Sci., USA,:804-1808 (April 1987). See also, J. H. Ohyashiki et al, Cancer Genet. Cytogenet., 25:341-350 (1987); H. D. Preisler et al, Cancer Research, 47:874-880 (Feb. 1987); C. W. Rettenmier et al, J. Cell. Biochem., 33:109-115 (1987); and R. Sacca et al, Proc. Natl. Acad. Sci. USA, 82:3331-3335 (1986). The product of the c-fms proto-oncogene is believed to be related to, and possibly identical with, a receptor of macrophage colonystimulating factor (M-CSF). See, e.g., C. J. Sherr et al, Cell, 41:665-676 (1985);

There remains a need in the treatment of such cancers for therapeutic products capable of destroying the carcinoma cells without severely adversely affecting the patient otherwise.

BRIEF DESCRIPTION OF THE INVENTION

As one aspect of the invention there is provided a composition for treating cancers which are characterized by high level expression of the c-fms proto-oncogene/M-CSF receptor gene. The composition includes M-CSF polypeptide (or the active fragment thereof) crosslinked to a cytotoxic agent, which is capable of crossing the membrane, of the cell bearing the c-fms gene product/M-CSF receptor and acting in the cytoplasm to destroy the cell. Preferred cytotoxic agents include A and B chain toxins, A chain toxins and genetically engineered toxins.

Still a further aspect of the invention involves a method for making the M-CSF/cytotoxic agent composition. The M-CSF and toxin may be linked by employing one or more heterofunctional or bifunctional protein cross linkers or by genetic fusion. The bifunctional cross-linkers are chosen to ensure that the M-CSF/toxin composition is stable while the composition is homing to the target cell. At the same time the crosslinker has to permit the release of the toxin portion after the M-CSF/toxin composition has entered the cell. See, e.g. *Molecular Action of Toxins and Viruses.* P. Cohen and S. van Heyningen, eds., Elsevier, N.Y., pp51-105 (1982).

As another aspect there is disclosed a method for treating cancers characterized by an over-expression of the c-fms protooncogene/M-CSF receptor gene. This method involves regionally administering to the in vivo site of such a cancer, the composition of the invention, or, alternatively, administering the composition in an ex vivo purging treatment of a mixture of cells. The composition acts by attaching to the c-fms protein on the carcinoma and delivering the toxin through the cell membrane, where the toxin destroys the cell. Among such receptor overexpressing cancers are acute myelocytic leukemia, ovarian carcinoma, lung carcinoma, and those recited above.

Other aspects and advantages of the present invention will be apparent upon consideration of the following detailed description of the invention, including illustrative examples of the practice thereof.

BRIEF DESCRIPTION OF THE DRAWINGS

FIG. 1 illustrates a DNA and amino acid sequence for an M-CSF polypeptide.

DETAILED DESCRIPTION OF THE INVENTION

The therapeutic composition of the invention is a conjugate of M-CSF, which is capable of binding to the c-fms protooncogene/M-CSF receptor gene product on certain cancer cells, and a cytotoxic agent capable of being transported through the cell membrane and acting in the cytoplasm to destroy the cell.

The M-CSF for use in the present invention may be recovered from natural sources and purified. (See e.g, UK Patent 2,016,477 and PCT published application WO86/04587). Alternatively, the M-CSF may be produced recombinantly. One possible recombinant M-CSF polypeptide useful in the present invention has been described in PCT published application WO86/04607. Another M-CSF polypeptide is described in co-pending, co-owned U.S. patent application Ser. No. 940,362 and in G. G. Wong et al, Science, 235:1504-1508 (1987). The amino acid and DNA sequence of the M-CSF described therein is presented hereto in FIG. 1. Other forms of M-CSF bearing the active site thereof may also be employed in this composition, including synthetically produced polypeptides or polypeptides modified by recombinant means.

The term "M-CSF" is herein defined as including the naturally occurring human polypeptide M-CSF and naturally-occurring allelic variations of the polypeptide. Allelic variations are naturally-occurring base changes in the species population which may or may not result in an amino acid change in a polypeptide or protein. Additionally included in this definition are both recombinant and synthetic versions of the polypeptide M-CSF, which may contain induced modifications in the peptide and DNA sequences thereof.

For example, the M-CSF polypeptide in the composition of the present invention may be characterized by a peptide sequence the same as or substantially homologous to the amino acid sequence illustrated in FIG. 1. These sequences may be encoded by the DNA sequence depicted in FIG. 1 or sequences containing allelic variations in base or amino acid sequence or deliberately modified structures coding for polypeptides with M-CSF biological properties.

Synthetic M-CSF proteins for use in the composition of the present invention may wholly or partially duplicate continuous sequences of the amino acid residues of FIG. 1. These sequences, by virtue of sharing structural and conformational characteristics with M-CSF polypeptides, e.g., the active site of the polypeptide of FIG. 1, may also possess M-CSF biological properties. Thus synthetic or recombinant polypeptides or fragments thereof may also be employed as biological or immunological equivalents for M-CSF polypeptides in the composition and methods of the present invention.

M-CSF, as used in the present invention also includes factors encoded by sequences similar to FIG. 1, but into which modifications are naturally provided or deliberately engineered. Modifications in the peptide or sequence of M-CSF can be made by one skilled in the art using known techniques. Specific modifications of interest in the M-CSF related sequences may include the replacement of one or more of the nine cysteine residues in the coding sequence with other amino acids. Preferably several cysteines in each sequence are replaced with another amino acid, e.g. serine, to eliminate the disulfide bridges at those points in the protein. For example, lysine at amino acid position 163 (FIG. 1) could be deleted or substituted with another amino acid in order to eliminate the sensitivity of this region of M-CSF to trypsin-like proteases. Mutagenic techniques for such replacement are well known to one skilled in the art. [See, e.g., U.S. Pat. No. 4,518,584.]

Other specific mutations of the sequence of M-CSF described herein involve modifications of one or more of the glycosylation sites in the sequence. The absence of glycosylation or only partial glycosylation results from amino acid substitution or deletion at one, two, three or all of the asparagine-linked glycosylation recognition sites present in the sequence of M-CSF. The asparagine-linked glycosylation recognition sites comprise tripeptide sequences which are specifically recognized by appropriate cellular glycosylation enzymes. These tripeptide sequences are either asparagine-X-threonine or asparagine-X-serine, where X is usually any amino acid. A variety of amino acid substitutions or deletions at one or both of the first or third amino acid positions of a glycosylation recognition site (and/or amino acid deletion at the second position) results in non-glycosylation at the modified tripeptide sequence. Modification and variation of the types of oligosaccharides which attach to the O or N-linked glycosylation sites can occur by production of the sequence in either mammalian, bacterial, yeast or insect cells. Such modifications in the proteins are also encompassed by the term M-CSF.

Yet further modifications of M-CSF polypeptides may employ sequences which are designed for improved pharmacokinetics, by, e.g., association with polyethylene glycol. Alternatively, the last 25 to 35 amino acids of the mature protein can be eliminated by appropriate gene deletion techniques to provide another form of M-CSF for use in the present invention. Such a deleted M-CSF may have use in genetic fusion to a cytotoxic agent. Amino acid residues 464 to 485 comprise a potential hydrophobic membranepenetrating region. An M-CSF molecule that contains this sequence may desirably be employed in the composition of the invention, because these residues may embed the conjugate in the cell membrane, thereby aiding in the transfer of the cytotoxic agent into the cytosol.

An exemplary DNA sequence for the production of various M-CSF peptides have been deposited with the American Type Culture Collection, 12301 Parklawn Drive, Rockville, MD. The cDNA sequence illustrated in FIG. 1 below in vector p3ACSF-69, included in E. coli HB101 has been deposited on April 16, 1986 and given accession number ATCC 67092.

The cytotoxic agent linked to the M-CSF polypeptide is preferably a toxin or chemical agent which is capable of acting in the cytoplasm. Toxins may be employed which have a translocation property to move it through the cell membrane and a cytolytic domain, which provides its killing ability. One preferable class of toxins well-suited for this composition consists of two functionally different parts, termed A and B, which are connected by a disulfide bond. The A chain portion contains the enzymatic activity that enters the cytosol and kills the cell. The B chain moiety is responsible for binding of the toxin to the cell and presumably contains a domain that aids the A chain in crossing the cell membrane. Exemplary toxins for such use include native or genetically engineered ricin, abrin, modeccin, viscumin, *Pseudomonas aeruginosa* exotoxin, Diphtheria toxin, Cholera toxin, *Shigella* toxin and *E. coli* heat labile toxin. The toxin portion of a conjugate prepared according to the invention can consist of the cytotoxic A chain portion only, the native holotoxin, or an engineered holotoxin, i.e., a toxin lacking its lectin binding property.

Other toxins which have only a single chain (an A chain portion) may also be employed. Examples of these toxins are ribosome inactivating proteins, such as pokeweed antiviral protein and gelonin. See, L. Barbieri et al, *Cancer Surveys*, 1:489–520 (1982) for a more complete list of ribosome inactivating proteins.

Mutant toxins or genetically engineered toxins may also be employed. Additionally microbially produced cytotoxic agents, and other non-protein organic molecules may be used as cytotoxic agents. The M-CSF ligand can also be linked to cytotoxic drugs, such as anthracyclines, e.g., doxorubicin, daunomycin, and the vinca alkaloids, such as, vindesine, vinblastine, vincristine. Methotrexate and its derivatives may also be employed as cytotoxic agents. More effective agents are those in which many molecules (between 5 to 50) of the drug are linked to the M-CSF through a polymer carrier, e.g., dextran. Bonds linking the drug to the carrier should be cleavable by the chemical environment inside the cell.

The M-CSF and a cytotoxic agent may be linked in a variety of ways. One way of linking these components is by employing one or more standard bifunctional protein crosslinkers, such as succinimidyl 3-(2-pyridyldithio)propionate (SPDP) or succinimidyl acetyl-thiopropriate (SATP). These crosslinkers form stable disulfide bonds between the M-CSF and toxin, or other cytotoxic agent, and yet are capable of releasing the toxin portion of the composition inside the cell, due to cleavage of the disulfide bonds by chemicals inside the cell, e.g., intracellular glutathione. These linking methods are known to those skilled in the art. See, e.g., J. Carlsson et al, *Biochem. J.*, 173:723–737 (1978) and N. Fujii et al, *Chem, Pharm. Bull.*, 33:362–367 (1985). See also, A. J. Cumber et al, *Methods Enzymol.*, 112:207–225 (1985) for other general methods for conjugating toxins to proteins.

For example, one method according to the invention involves making a M-CSF-toxin composition, using a toxin having both and A and B chain. The method involves the steps of:

(a) reacting the M-CSF with sufficient crosslinker to introduce between 1 to 6 reactive groups per molecule of M-CSF. A sufficient amount of crosslinker which can be used for this purpose is between approximately 6 to 50 moles of crosslinker per mole of M-CSF dimer.

(b) reacting a toxic protein having A and B chain subunits connected by at least one disulfide bond with a conventional reducing agent, thereby liberating the chains from each other.

(c) reacting the derivitized M-CSF of step (a) with the liberated A chain subunit of the reduced toxin; and (d) separating from the reaction mixture conjugates comprising M-CSF linked by disulfide bonds to A chain subunits. One exemplary growth factor/toxin conjugate is prepared by this method, modifying M-CSF with SPDP, followed by conjugation of ricin A chain toxin via a disulfide bond.

Another method for making the compositions of the present invention involves the following steps:

(a) reacting the M-CSF with sufficient crosslinker to introduce between 1 to 6 reactive groups per molecule of M-CSF;

(b) reacting the derivatized M-CSF of step (a) with a holotoxin having A and B subunits attached by at least one disulfide bond, the holotoxin being functionalized with a protein crosslinker which is preferably attached to the B subunit; and (c) separating a conjugate formed by M-CSF becoming attached to the B subunit from free M-CSF and toxin in the reaction mixture.

Another manner of linking the components of the composition of the present invention is by a genetic fusion method. See, for example, U.S. Pat. No. 4,675,382.

The compositions of the present invention containing both M-CSF and a toxin can be employed in methods for treating cancers characterized by over-expression of the c-fms proto-oncogene/M-CSF receptor gene. Among such cancers are acute myelocytic leukemia, ovarian cancer, breast cancer, lung cancer, pancreatic cancer and renal cancer. The composition of the invention operates by the targeting of the c-fms proto-oncogene by the M-CSF portion of the composition. Once attached to this receptor, the M-CSF molecule aids in transporting the cytotoxic agent through the cell membrance and into the cytosol. Inside the cell, the bonds linking the cytotoxic agent to the M-CSF are cleaved by chemicals naturally within the cell and the agent is released to kill the cancer cell.

The composition of the present invention can be administered in a variety of ways. Desirably the composition is administered regionally in vivo, to the site of the carcinoma. For example, it can be administered interperitonially, if desired, to contain its distribution to the peritoneum for use in treating a suitable cancer, e.g., ovarian cancers. Similarly for treating lung cancers, the composition could be delivered in the form of an inhalant. If desirable, the composition may be administered subcutaneously, such as bathing effected tissue after surgical removal of a tumor e.g., for breast cancers. Additionally, the composition can be employed in ex vivo applications, such as "purging" of a mixture of cells removed from a patient, for patients having a systemic cancer which is not appropriate for regional application. The treatment of patients with acute myelocytic leukemia, for example, could involve removal of bone marrow cells from the body. These cells are then treated outside the body with the composition of the present invention to destroy a subset of these cells which are overexpressing the c-fms protooncogene. The "purged" cells are then reintroduced into the patient. The M-CSF/toxin composition of the invention can thereby serve as a purging agent to destroy the leukemic cells in the bone marrow of AML patients about to undergo autologous bone marrow transplantation Other ex vivo purging treatments may also employ the composition of the invention.

The therapeutic composition for use in this invention may be in the form of a pyrogen-free, parenterally acceptable aqueous solution. The preparation of such a parenterally acceptable protein solution, having due regard to pH, isotonicity, stability and the like, is within the skill of the art.

The dosage regimen involved in treating the patient with the composition according to this invention will be determined by the attending physician considering various factors which modify the action of drugs, e.g. the condition, body weight, sex and diet of the patient, the severity of any infection, time of administration and other clinical factors. Additionally, the mode of administration could effect the dosage, e.g., ex vivo or in vivo. Generally, the daily regimen should be in the range of 2 to 2000 micrograms of polypeptide per kilogram of body weight.

The following examples illustrate the production of the M-CSF polypeptide and the construction of an M-CSF/toxin conjugate of the present invention.

EXAMPLE 1

Recombinant Production of M-CSF

To express the recombinant M-CSF polypeptide by recombinant means, the DNA encoding the polypeptide is transferred into an appropriate expression vector and introduced into selected host cells by conventional genetic engineering techniques.

Mammalian cell expression vectors for production of M-CSF, such as p3ACSF-69, may be synthesized by techniques well known to those skilled in this art. The components of the vectors, e.g. replicons, selection genes, enhancers, promoters, and the like, may be obtained from natural sources or synthesized by known procedures See, Kaufman et al, *J. Mol. Biol.*, 159:511–521 (1982); and Kaufman, *Proc. Natl. Acad. Sci., U.S.A.*, 82:689–693 (1985). Suitable cells or cell lines for the expression of these recombinant M-CSF proteins may be Chinese hamster ovary cells (CHO), monkey COS-1 cells or CV-1 cells. The selection of suitable mammalian host cells and methods for transformation, culture, amplification, screening and product production and purification are known in the art. See, e.g., Gething and Sambrook, *Nature*, 293:620–625 (1981), or alternatively, Kaufman et al, *Mol Cell. Biol.*, 5(7):1750–1759 (1985) or Howley et al, U.S. Pat. No. 4,419,446. Other exemplary mammalian host cells include particularly primate cell lines and rodent cell lines, including transformed cell lines. Normal diploid cells, cell strains derived from in vitro culture of primary tissue, as well as primary explants, are also suitable. Candidate cells need not be genotypically deficient in the selection gene so long as the selection gene is dominantly acting. For stable integration of the vector DNA, and for subsequent amplification of the integrated vector DNA, both by conventional methods, CHO cells may be employed. Other suitable mammalian cell lines include but are not limited to, HeLa, mouse L-929 cells, 3T3 lines derived from Swiss, Balb-c or NIH mice, BHK or HaK hamster cell lines.

Stable transformants are then screened for expression of the product by standard immunological or enzymatic assays. The presence of the DNA encoding the variant proteins may be detected by standard procedures such as Southern blotting. Transient expression of the DNA encoding the variants during the several days after introduction of the expression vector DNA into suitable host cells such as COS-1 monkey cells is measured without selection by activity or immunologic assay of the proteins in the culture medium. The transformation of these vectors into appropriate host cells can result in expression of the M-CSF.

Similarly, one skilled in the art could manipulate the sequence of FIG. 1 by eliminating or replacing the mammalian regulatory sequences flanking the coding sequence with bacterial sequences to create bacterial vectors for intracellular or extracellular expression of M-CSF by bacterial cells. The DNA encoding the factor may be further modified to contain different codons for bacterial expression as is known in the art. Preferably the sequence is operatively linked in-frame to a nucleotide sequence encoding a secretory leader polypeptide permitting bacterial expression, secretion and processing of the mature variant protein, also as is known in the art. The compounds expressed in bacterial host cells may then be recovered, purified, and/or characterized with respect to physicochemical, biochemical and/or clinical parameters, all by known methods. For example, the M-CSF coding sequence could be inserted into a known bacterial vector using procedures such as described in T. Taniguchi et al., *Proc. Natl Acad. Sci. USA*, 77:5230–5233 (1980). This exemplary bacterial vector could then be transformed into bacterial host cells and the factor expressed thereby. The various strains of *E. coli (e.g., HB*101, MC106) are well-known as host cells in the field of biotechnology. Various strains of *B. subtilis, Pseudomonas,* other bacilli and the like may also be employed in this method. For a strategy for producing extracellular expression of such factors in bacterial cells, see, e.g. European patent application EPA 177,343.

Similar manipulations can be performed for the construction of an insect vector [See, e.g., procedures described in published European patent application 155,476] for expression in insect cells. See, e.g. Miller et al, *Genetic Engineering*, 8:277–298 (Plenum Press 1986) and references cited therein.

A yeast vector could also be constructed employing yeast regulatory sequences for intracellular or extracellular expression of M-CSF by yeast cells. Many strains of yeast cells known to those skilled in the art are also available as host cells for expression of the polypeptides useful in the invention. [See, e.g., procedures described in published PCT application WO 86 00639 and European patent application EP 123,289.]

EXAMPLE 2

An M-CSF Toxin Conjugate

For construction of an M-CSF toxin conjugate according to the invention, the growth factor M-CSF was produced in mammalian cells as described in pending U.S. patent application Ser. No. 940,362, the disclosures of which are incorporated by reference herein, and G. G. Wong et al, *Science*, 235 *supra.* 100 micrograms (1.1 nanomoles) M-CSF in 100 millimolar $NaHCO_3$ (425 microliters) was reacted with SPDP (27.5 nanomoles) in dimethylformamide (DMF). The reaction was allowed to proceed for five hours at 4 degrees Celsius to introduce approximately four to six sulfhydryl groups per molecule of M-CSF dimer. The derivatized growth factor was then reacted with freshly reduced ricin A chain (obtained by the standard method of S. Ramakrishnan et al, *Biochim. Biophys. Acta*, 719: 341–348 (1982); and A. J. Cumber et al, supra) (10 nanomoles). The disulfide bond was allowed to form overnight at 4 degrees Celsius. The resulting M-CSF-ricin A chain conjugate was separated from excess ricin A chain by gel filtration on a Sepherogel ™ TSK-3000 high pressure liquid chromatography column.

Two portions of the conjugate were analyzed on a gradient SDS gel and the protein bands were visualized with Western methodology employing either an anti-ricin A chain or an anti-M-CSF antibody, both obtained by conventional immunological techniques. Each antibody visualized the same conjugate bands which represent molar rations of M-CSF:ricin A chain of 1:1 to 1:5. Ricin A chain dimer is removed on a Mono Q column and residual M-CSF is eliminated with a Blue Sepharose column.

Numerous modifications may be made by one skilled in the art to the methods and components of the present invention in view of the disclosure herein. Such modifications are believed to be encompassed in the appended claims.

What is claimed is:

1. A therapeutic composition for treating carcinoma characterized by over-expression of the c-fms proto-oncogene/M-CSF receptor gene comprising a M-CSF polypeptide conjugated to a cytotoxic agent and a pharmaceutical carrier therefor.

2. The composition according to claim 1, wherein said cytotoxic agent is a toxin selected from the group comprising double-chain ricin, ricin A chain, abrin, abrin A chain, modeccin and modeccin A chain, *Pseudomonas aeruginosa* exotoxin, Cholera toxin, *Shigella* toxin, *E. coli* heat labile toxin and Diptheria toxin.

3. The composition according to claim 1 where said M-CSF polypeptide is linked to said cytotoxic agent by a heterofunctional protein cross linking agent.

4. The composition according to claim 3 where said cross linking agent is selected from the group consisting of succinimidyl 3-(2-pyridyldithio)propionate) or succinimidyl acetylthiopropriate.

5. The composition according to claim 1 comprising M-CSF linked through SPDP to a full ricin molecule.

* * * * *